United States Patent [19]
Douglas

[11] Patent Number: 5,292,344
[45] Date of Patent: Mar. 8, 1994

[54] PERCUTANEOUSLY PLACED ELECTRICAL GASTROINTESTINAL PACEMAKER STIMULATORY SYSTEM, SENSING SYSTEM, AND PH MONITORING SYSTEM, WITH OPTIONAL DELIVERY PORT

[76] Inventor: Donald D. Douglas, 2009 Madison Ave., Lewisburg, Pa. 17837

[21] Appl. No.: 911,703

[22] Filed: Jul. 10, 1992

[51] Int. Cl.$^5$ ............................................. A61N 1/32
[52] U.S. Cl. ..................................................... 607/40
[58] Field of Search ............. 128/780, 421, 422, 642, 128/419 R, 639, 733, 898, 734, 419 PG

[56] References Cited

U.S. PATENT DOCUMENTS

| | | | |
|---|---|---|---|
| 3,411,507 | 11/1968 | Wingrove | 128/422 |
| 3,911,930 | 10/1975 | Hagfors et al. | 128/422 |
| 4,981,470 | 1/1991 | Bombeck, IV | 128/780 |
| 5,109,870 | 5/1992 | Silny et al. | 128/642 |

OTHER PUBLICATIONS

J. C. Eagon and K. A. Kelly, Effect of Electrical Stimulation on Gastric Electrical Activity, Motility and Emptying. *Gastro*, 102, A833, 1992.

B. W. Miedema, et al., Pacing the Human Stomach, *Surgery*, vol. 111, No. 2, Feb. 1992, pp. 143-150.

A. Sawchuk, et al., Electrical Pacing of the Roux Limb Resolves Delayed Gastric Emptying, *Journal of Surgical Research*, vol. 42, No. 6, Jun. 1987, pp. 635-641.

B. Bellahséne, et al., Acceleration of Gastric Emptying with Electrical Stimulation in a Canine Model of Gastroparesis, *American Journal of Physiology*, vol. 262, pp. G826-G834, 1992.

Waldhausen et al., "Postoperative Pacing for Gastric Antral Distension" (Abstract), *Gastrointestinal Motility*, 1989, p. 1:66.

*Primary Examiner*—William E. Kamm
*Assistant Examiner*—George Manuel
*Attorney, Agent, or Firm*—Mason, Fenwick & Lawrence

[57] ABSTRACT

The present invention provides a system for delivering electrical impulses of suitable magnitude and frequency to the inner lining of the gastrointestinal tract. The system senses the motor activity of the intestinal tract, thus providing feedback as to the body's response to the imposed electrical stimulation. Further, the system monitors critical parameters of gastrointestinal luminal contents, such as pH. Moreover, the system may include a delivery port for administration of fluids or materials to the gastrointestinal tract, and/or for removing fluids or materials from the gastrointestinal tract. Preferably, the system penetrates the skin surface and the inner lining of the gastrointestinal tract, in the stomach, intestine, or colon. The invention provides embodiments which can be adapted for easy removal for placement on a short-term basis, as well as embodiments having a longer-lasting design for placement on a relatively permanent basis.

30 Claims, 3 Drawing Sheets

PERCUTANEOUSLY PLACED ELECTRICAL GASTROINTESTINAL PACEMAKER STIMULATORY SYSTEM, SENSING SYSTEM, AND PH MONITORING SYSTEM, WITH OPTIONAL DELIVERY PORT

BACKGROUND OF THE INVENTION

1. Field of the Invention

The present invention relates to pacemakers and monitoring systems. More specifically, the invention relates to a gastrointestinal pacemaker stimulatory system that is able to sense and variably pace motor activity of the intestinal tract, having an optional delivery/removal port for administration or removal of fluids or recording systems, suitable for use in humans and in animals.

2. Related Art

The gastrointestinal tract is responsible for an essential step in the digestive process, the reception of nutrition in the human body. Nutrition is received by absorbing mucosa in the gastrointestinal tract, using a very complex mechanism. An important element of the digestive process is intestinal peristalsis, the coordinated and self-regulated motor activity of the intestinal tract. Peristalsis is accomplished through a coordinated combination of electrical, chemical, and hormonal mediation, possibly in addition to other unknown mechanisms.

It is known that many diseases and maladies can affect the motor activity of the gastrointestinal tract, causing malfunction of the digestive process. Such diseases include diabetesmellitus, scleroderma, intestinalpseudo-obstruction, ileus, and idiopathic gastroparesis. Other maladies such as tachygastria or bradiagastria can also hinder coordinated muscular motor activity of the bowel.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Whereas some of these disease states can be corrected by medication or by simple surgery, in most cases treatment with drugs is not adequately effective, and surgery often has intolerable physiologic effects on the body.

It is known that motor activity can be recorded as electrical activity of the muscle. Traditionally, motor activity has been measured using recording electrodes placed directly on the muscle of the intestinal tract, or on the skin external to the intestinal tract. For example, electrocardiograms measure the electrical activity of the heart in this manner.

Presently, however, there is no known endoscopically or surgically placed device to stimulate, record, or intelligently alter the muscular contractions of the intestinal muscles from the intraluminal mucosa of the intestinal tract for the purpose of interventional electrical medical therapy, thereby efficaciously altering movement of nutrients through the intestinal tract. Therefore, there is a need in the art for a system and method to properly pace intestinal motor activity for correcting ineffective or absent propulsive electrical muscular activity of the gastrointestinal tract.

3. Medical Background

Normal Gastric Pacemaker Activity. The normal contractile activities of the stomach are coordinated and controlled by myoelectrical activities, termed electrical control activity or pacesetter potentials [Ref. 1]. The normal gastric pacemaker rhythm in man is approximately 3 cpm (cycles per minute), with the normal range generally considered to be from 2.5-3.6 cpm [Refs. 2-4]. The underlying mechanisms which control and modulate the pacesetter potential [Ref. 1] will not be discussed here.

Abnormal Gastric Pacemaker Activity. Abnormal gastric pacemaker activities have been detected in numerous clinical conditions: diabetic and idiopathic gastroparesis [Refs. 5,6], dyspepsia [Ref. 7], intestinal pseudo-obstruction [Ref. 8], eating disorders [Ref. 9], nausea and gastric ulceration [Ref. 10], nausea of pregnancy [Ref. 11], and motion sickness [Ref. 12]. Most of these conditions are associated with gastric disorders and symptoms of nausea, indigestion, vague epigastric distress, anorexia and vomiting.

Tachygastrias are abnormally fast gastric dysrhythmias ranging from 3.6-9.9 cpm [Refs. 11, 12]. Bradygastrias are abnormally slow gastric dysrhythmias ranging from 1-2.5 cpm [Ref. 13]. Arrhythmias are flatline signals in which no discernible waves are detected [Ref. 11]. These gastric dysrhythmias have been detected non-invasively with cutaneous electrodes as well as with invasive methods using mucosal or serosal electrodes [Refs. 4, 14, 15].

TABLE 1 (below) lists clinical entities in which gastric dysrhythmias have been detected. Many of these entities are chronic ailments which are poorly understood. The gastropareses in particular are thought to be neuromuscular diseases of the stomach which result in delayed gastric emptying and the typical symptoms of nausea, anorexia and vomiting. These entities often respond poorly to drug therapy.

However, in certain individuals with chronic symptoms and gastric dysrhythmias, pharmacological therapy has resulted in eradication of the gastric dysrhythmias and re-establishment of the normal 3 cpm gastric pacemaker rhythm [Ref. 5]. In diabetic patients with gastroparesis, the re-establishment of 3 cpm pacemaker rhythms was associated with the reduction in symptoms, but gastric emptying was not improved. The concept has been proposed that the presence of a normal 3 cpm gastric rhythm is more important to improvement in symptoms than the rate of gastric emptying per se [Ref. 5].

Applicant infers from recent reports [Ref. 4] that pacing the human stomach is feasible. Pacing has been considered with respect to symptoms and gastric emptying in several patients with post-operative distention or gastroparesis [Refs. 16, 17]. However, the stimulus parameters for gastric pacing are not worked out.

In review of the medical and surgical literature, the only known way pacing of the human stomach has involved placement of cardiac pacing wires into the muscle layers of the stomach at the time of laparotomy. The laparotomies were performed primarily for cholecystectomy or for placement of a feeding tube in the jejunum.

There is apparently no known method for convenient placement of pacemaker wires or electrodes for recording gastric myoelectrical activity from the gastric mucosa. A system for the percutaneous and endoscopic placement of such a system would thus be a novel advance for pacing the stomach's electrical activity or for recording myoelectrical activity from the stomach. The present invention offers these possibilities in a safe, quick and convenient package.

TABLE 1
GASTRIC DYSRHYTHMIAS ASSOCIATED WITH CLINICAL CONDITIONS

Tachygastrias (4–9.9 cpm myoelectrical pattern)
1. Gastroparesis (Diabetic, Idiopathic, Ischemic)
2. Intestinal pseudo-obstruction
3. Nausea of pregnancy
4. Functional dyspepsia -dysmotility type with normal gastric emptying*
5. Gastric ulcers (acute) with nausea
6. Postoperative
   Acute post-op with ileus
   Post-cholecystectomy
   (Roux-en-Y reconstructions 10–13 cpm small bowel frequencies)
7. Eating disorders - anorexia nervosa
8. Premature infants
9. Drug-induced (Glucagon, Epinephrine, Morphine sulfate)
10. Functional (idiopathic) dyspepsia - dysmotility type Tachyarrhythmias (mix of tachygastrias and bradygastrias)
1. Motion sickness
2. Idiopathic gastroparesis Bradygastrias (1–2 cpm myoelectrical pattern)
1. Gastroparesis (Diabetic, Idiopathic, Ischemic, Post-operative (gastric resection))
2. Intestinal pseudo-obstruction
3. Nausea of pregnancy
4. Functional dyspepsia - dysmotility type with normal gastric emptying*
5. Eating disorders - bulimia nervosa
6. Drug-induced
   Epinephrine Arrhythmias (flatline EGG pattern)
1. Nausea of pregnancy
2. Hyperemesis gravidarum
3. Drug-induced - epinephrine
4. Bilroth I or II with gastroparesis
5. Bilroth I or II with no symptoms (normal 3 cpm EGG pattern)

*Normal 3 cpm EGG pattern is seen in obstructive gastroparesis
**Normal 3 cpm EGG pattern is seen in functional dyspepsia - reflux type

SUMMARY OF THE INVENTION

The present invention provides electrical gastrointestinal pacemaker with a variety of different advantageous features in various combinations. For example, the present invention provides a system for delivering electrical impulses of suitable magnitude and frequency to the inner lining of the gastrointestinal tract. According to another aspect of the invention, the invention provides means for sensing the motor activity of the intestinal tract, thus providing feedback as to the body's response to the imposed electrical stimulation. Further, the invention provides for monitoring critical parameters of gastrointestinal luminal contents, such as pH. Moreover, the invention provides for a delivery port for administration of fluids or materials to the gastrointestinal tract, and/or for removing fluids or materials from the gastrointestinal tract.

These features of the various embodiments of the invention are advantageously provided in a system that penetrates the skin surface of the body and the inner lining of the gastrointestinal tract, in the stomach, intestine, or colon. The invention provides embodiments which can be adapted for easy removal for placement on a short-term basis, as well as embodiments having a longer-lasting design for placement on a relatively permanent basis.

The efficacy of the invention is enhanced by using an adjustable electrical current source, preferably in combination with a means for administering the electrical current in pulses at a variable, controllable rate. Further, the efficacy of the invention may be monitored in real time using any or all of a variety of sensors, such as electrical sensors for measuring muscular electrical activity, the pH of the intestinal contents, and the pressure gradient within the gastrointestinal lumen generated during stimulated muscular activity.

Other objects, features, and advantages of the present invention will become apparent on reading the following Detailed Description in conjunction with the accompanying drawing figures.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
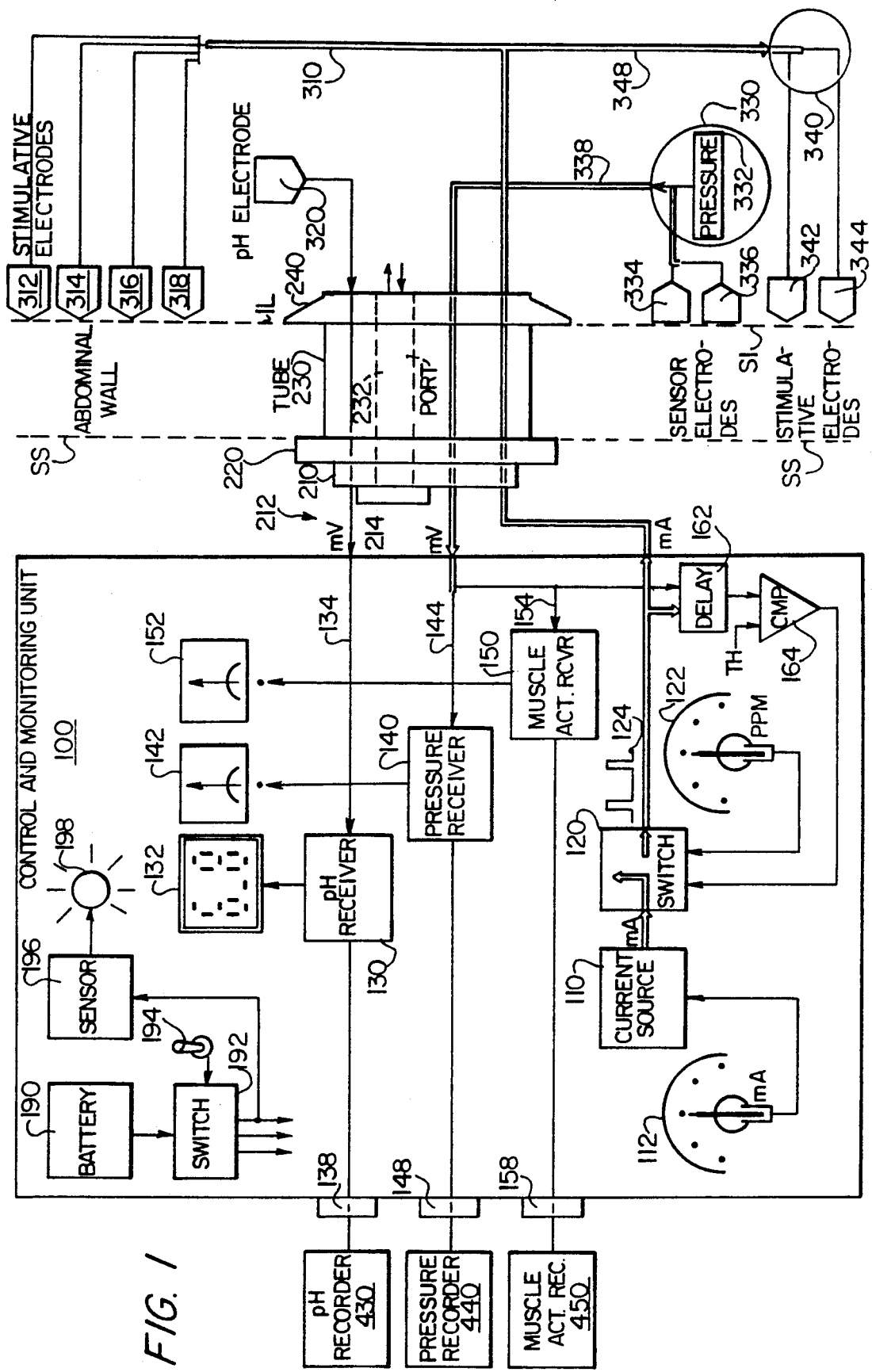
FIG. 1 is a schematic block diagram indicating various components in a comprehensive embodiment of the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

Patients with many of the entities listed in TABLE 1 are potential candidates for a system according to the present invention, particularly when the gastric motility/gastric dysrhythmia disorders are chronic, severe, and/or recalcitrant to medical therapies. These gastric disorders may be treated with drugs, but in many instances a non-pharmacologic management may be preferred. Under some conditions, drug therapy is almost always ineffective (post-partial gastrectomy gastroparesis) and pacemaker therapy may be ideal for such patients.

Successful pacing at the normal 3 cpm frequency should reduce patients' symptoms. Gastric emptying also may be improved to some extent depending upon the underlying condition of the gastric smooth muscle.

In addition, the present invention offers the possibility of delivering virtually any drug or nutrient solution required for patient care. The system also offers the capacity for gastric pacing and for recording gastric myoelectrical activity, depending upon the needs of the patients.

Finally, in addition to clinical uses the present invention may be used in a variety of animal and human research settings in which gastric contractions, gastric myoelectrical activity, gastric pacing and gastric pH are measured in response to selected stimuli. Furthermore, the inventive device may be used to pace the small intestine or colon in patients who have some disease that causes ineffective and non productive intestine peristalsis.

Referring generally to the drawing figures, a tube 230 penetrates the skin surface SS and is held in position against the inner lining IL of the gastrointestinal tract. The tube 230 is preferably made of a flexible, medically acceptable plastic polymer or composite material.

An inner fixative device 240, preferably made of a soft plastic polymer or other medically acceptable non-irritating material is provided to ensure that the device is not accidentally removed. In embodiments which are designed for easy removal, the inner fixative device 240 is made soft and compressible. However, in embodiments which are to remain in place for longer periods of time, the inner fixative device 240 is made of a firmer and more durable medically acceptable material. According to a preferred embodiment of the present invention, the fixative device 240 is not sutured to the gastrointestinal mucosa, but is held stationary with respect to the mucosa by a lock member 220 which surrounds and holds tube 230 at its entry point into the skin surface SS.

Extending from the fixative device 240 are a number of stimulative electrodes 312, 314, 316, and 318, disposed at the ends of respective pre-bent and insulated tentacles. These electrodes are preferably bipolar electrodes (each having two electrodes). The stimulative electrode-bearing tentacles are preferably made of non-irritating, soft projectiles of prefabricated material that house wires leading to electrode tips.

In a preferred embodiment, three or four electrodes function as stimulative electrodes for the gastrointestinal tract. This plurality of electrodes are provided, to ensure that there will always be some contact between at least one of the stimulative electrodes and the gastrointestinal mucosa. The pre-bent shape of the electrode-varying tentacles causes them to bend backward toward the mucosal surface of the gastrointestinal tract, so that the tentacles and protruding electrodes must be soft and non-abrasive to the gastrointestinal mucosa. Further, the manner in which the tentacles are shaped should be, as illustrated, gently bending toward the mucosa and contacting it with the furthest tips of the electrodes.

Also illustrated is a pH electrode 320 at the end of a pH probe. The pH probe and electrode are also manufactured of a medically acceptable, soft material, although the pH electrode is placed so that it does not touch the mucosa of the gastrointestinal tract.

Also extending from the fixative device 240 is an elongated soft tubing 338 connected to a soft, expanded polymer tip 330. A pressure transducer 332 extends from tube 338, and is placed within a sensor bulb 330. Pressure transducer 332 transmits information representing the pressure activity of the motor complex generated by the muscular activity in the gastrointestinal tract. This pressure transducer 332 allows measurement of the gastrointestinal tract's response to electrode stimulation.

Inside the soft tubing 338 are electrical connections terminating in bipolar sensing electrodes 334, 336. Preferably, the sensing electrodes are designed to extend outward to touch the sides of the gastrointestinal tract, relaying information back to sensing equipment to be described below. The sensor bulb 330 itself floats freely in the distal gastrointestinal tract.

An optional second floating bulb 340 is placed at the end of an elongated soft tube 348. Two stimulative bipolar electrodes 342 and 344 extend therefrom, and stimulate lower portions of the gastrointestinal tract in the same manner that stimulative electrodes 312, 314, 316, 318 stimulate the stomach lining.

The wires leading from stimulative electrodes 312, 314, 316, 318, 342, 344, the wires from sensor electrodes 334, 336, and from pH electrode 320, as well as the sensor line from pressure transducer 332, pass through tube 230 to a terminal plug 210. Removably connected to terminal plug 210 is a cable, generally indicated as element 212. Cable wires corresponding to the aforementioned wires are schematically illustrated as elements 124, 134, 144, 164 within cable 212. Cable 212 leads to a small portable control and monitoring unit 100, which governs the control and monitoring of the various electrodes and sensors. Preferably, cable 212 is removably attachable to terminal plug 210, to allow easy removal or substitution of unit 100.

Control and monitoring unit 100 uses basic technology similar to that in a MEDTRONIC 5375 pulse generator, but applies the technology in a novel manner. According to the invention, control and monitoring unit 100 can have any or all of a wide variety of capabilities. Within control and monitoring unit 100 are various elements, not all of which need be present in any given embodiment.

A current source, schematically illustrated as element 110, is controlled by an external current adjusting means, illustrated as a knob 112. The output of current source 110 is input to a schematically illustrated current switch 120. An external manual pulse rate adjusting means, schematically illustrated as knob 122, determines the frequency of repetition of the current pulses which are output by current switch 120, in pulses per minute (PPM). Current pulses generated by the arrangement of current source 110 and current switch 120 pass along path 124 to stimulative electrodes 312, 314, 316, 318, in the stomach, and optional stimulative electrodes 342, 344 in the intestinal tract below the stomach.

Of course, the current pulses may be generated using other means, such as AC current sources which have controllable frequency-responsive outputs. For example, voltage-controlled oscillators which provide an output current waveform of suitable shape and frequency in response to a voltage input to it, may be employed. Thus, the illustration of current source 110 and switch 120 in FIG. 1 is very schematic in nature, emphasizing the separate control of magnitude and pulse frequency.

In addition to stimulative functions, various sensing functions are provided by unit 100.

For example, a pH receiver 130 receives information from pH electrode 320 along path 134. An optional pH display 132, here illustrated as a digital LCD or LED display, is provided on the outside of the unit. A connector plug 138 is provided to transmit pH measurements from pH receiver 130 to an external pH recording device 430, allowing a history of pH readings to be recorded for later analysis.

Similarly, pressure receiver 140 is provided, to receive pressure measurements from pressure transducer 332 passed along path 144. An optional pressure display device 142, here illustrated as an analog dial display, may be provided on the outer face of the unit. A plug 148 is provided to transmit pressure measurements history from pressure receiver 140 to an external pressure recording device 440, allowing a history of pressure readings to be recorded for later analysis.

Further, a muscular activity receiver 150 is provided, and receives sensed electrical muscular activity from sensor electrodes 334, 336 that are passed along path 154. An optional electrical muscle activity display 152 is provided on the exterior of the unit, and is illustrated as an analog dial display. A plug 158 is provided, to transmit electrical muscle activity from electrical muscle activity receiver 150 to an external electrical muscle activity recorder 450, for recording a history of muscle activity for later analysis.

According to an alternative embodiment of the present invention, a delay detector 162 and threshold comparator 164 are provided. The stimulative electrical pulses on path 124 constitute a first input to delay sensor 162. A second input to delay sensor 162 is connected to a sensing mechanism lower in the gastrointestinal tract, such as muscle activity sensing line 154.

During operation, delay sensor 162 determines the delay between an imposed stimulative electrical pulse on path 124, and any response thereto on path 154. If a certain amount of time has passed after the application of a stimulative pulse is greater than a certain time threshold TH, then comparator 164 causes switch 120 to apply another pulse. If no response is measured before expiration of a given time period greater than TH, delay sensor 162 times out, sending a timeout signal to comparator 164 so that comparator 164 activates switch 120. It is understood that elements 162, 164 are schematic in nature, and may be implemented using components other than those specifically suggested by the arrangement in FIG. 1.

As appreciated by those skilled in the art, elements 162, 164 complete a feedback loop. The feedback loop ensures that application of stimulative pulses to electrodes 312, 314, 316, 318 causes a measurable change in the small intestine SI. Sensor electrodes 334, 336 pass sensed contractions in the small intestine along path 154 to delay element 162. During operation, if an electrical impulse is not sensed within a certain time period, another stimulative pulse is automatically delivered, as schematically indicated by the input to switch 120. Thus, the arrangement of delay element 162 and comparator 164 serves to override the manual setting, in pulses per minute, of element 122.

In the event that a substantial number of pulses are caused by the arrangement of elements 162, 164, without any feedback from sensor electrodes 334, 336, additional action is required. For example, the magnitude of the current can be set to a higher level, using control element 112. The patient or the doctor can be alerted to the condition by a visual or auditory indicator (not illustrated).

Unit 100 is provided with an on-off switch 194 which controls application of power from battery 190 to the various unit components described above, via a power switch 192. Preferably, a "battery low" sensor 196 is provided, and illuminates a warning indicator 198 to alert the user that battery 190 needs to be recharged or replaced.

An optional feature of the present invention is a port 232 extending from the exterior of the body into the gastrointestinal tract, generally parallel to the various wires 124, 134, 144, 154. Port 232 is provided to allow fluids or materials to be delivered from outside the body into the gastrointestinal tract. Alternatively or additionally, port 232 can be used to remove fluids or materials from the gastrointestinal tract. A suitable means is provided for closing the port when administration or removal of material is not taking place, the means being indicated schematically by a plug 214.

Figure 2A:
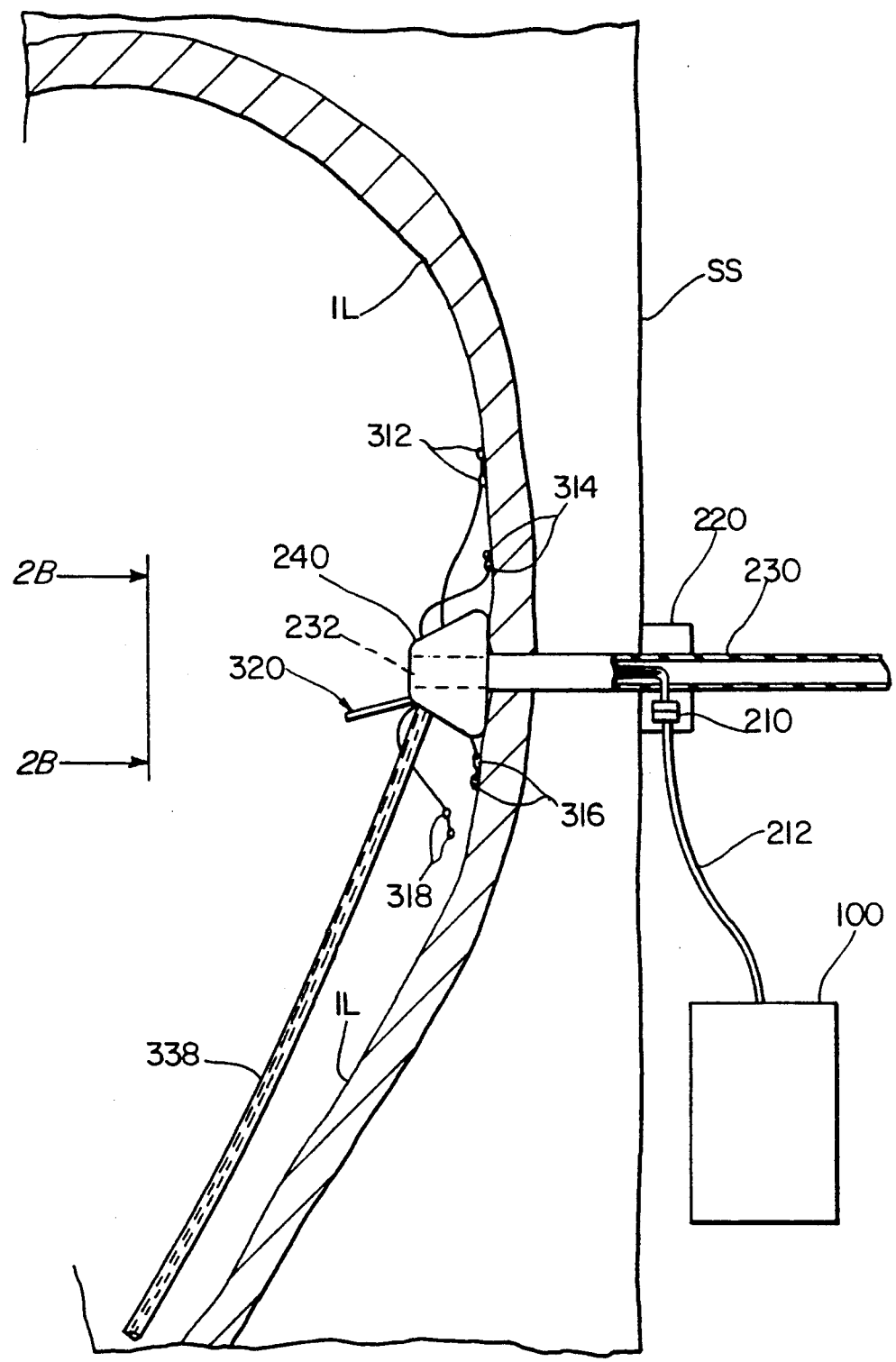
FIG. 2A is a side view of an embodiment of the present invention, as percutaneously deployed through an abdominal wall of a subject, with FIG. 2B being a view thereof as seen from a direction "2B" indicated in FIG. 2A.
Figure 2B:
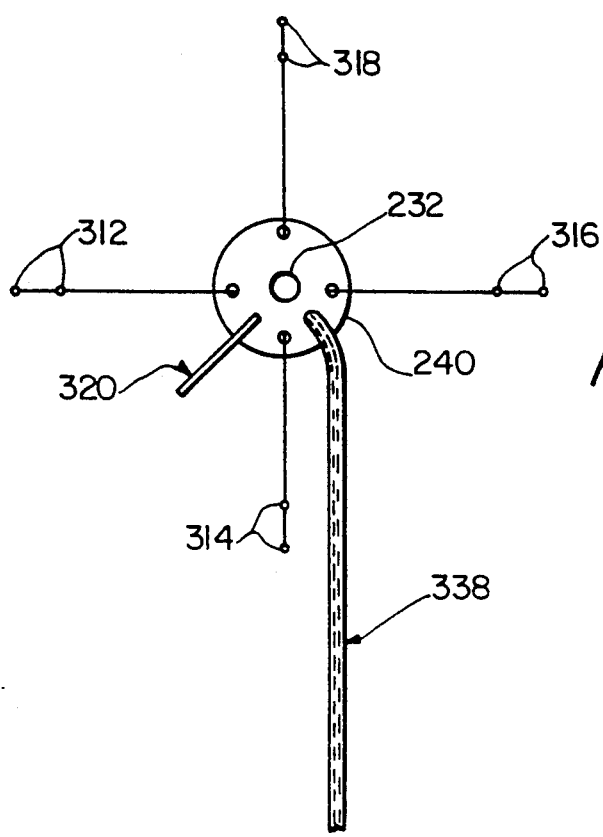
FIG. 2C is a side view of a lower portion of the embodiment than is illustrated in FIG. 2A, with FIG. 2C illustrating the portion extending from the stomach into the small intestine.
Figure 2C:
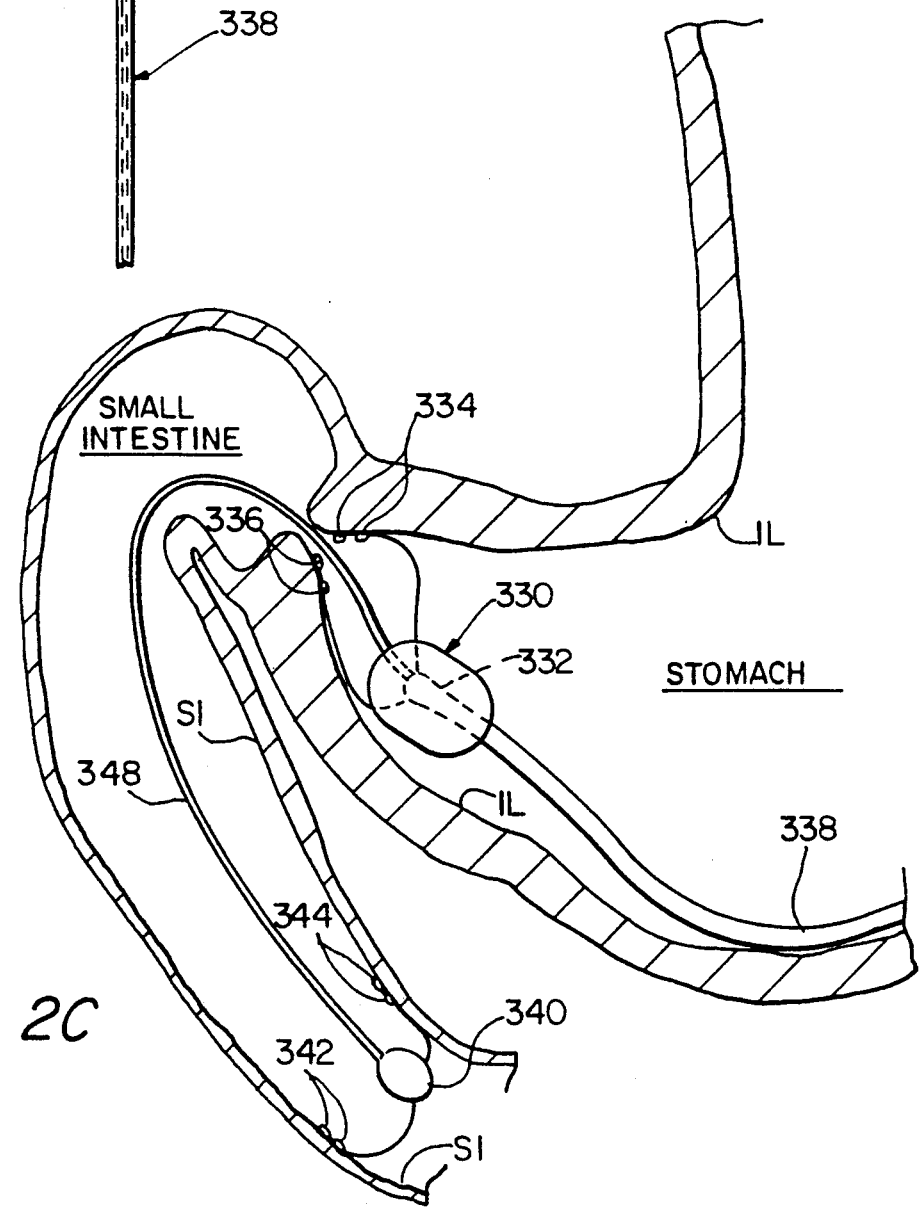

Tube 230 may either be a solid core polymer of medically soft and non-irritating material, or it may have a hollow core to form port 232. In one embodiment, tube 230 may be a short length of polymer that fits substantially flush with the skin surface SS. Alternatively, as shown in FIG. 2A, it may be a longer extension. It may be coiled outside the skin surface SS, allowing it to be taped to the skin surface SS. Control and monitoring unit 100, being a portable and detachable device, may be anchored to the body or skin surface by straps, an elastic holder around the waist area, or other suitable attachment means.

The components of the illustrated embodiment, with the exception of cable 212, control and monitoring unit 100, and external recording devices 430, 440, 450, may be inserted either surgically or endoscopically into the gastrointestinal tract. When using the endoscopic approach, using either fiber optic or video gastrointestinal endoscopes, elements of the present invention can be placed in the same way and using the same techniques as the placement of percutaneous enterogastrostomy tubes that are currently being used. An example of such placement technique is the BOWER PEG tube, and insertion and removal system, from a THEREMEDICS, INC., COREPACK, INC., Wheeling, Ill. 60090. Like other known systems and devices, the BOWER PEG tube and delivery system are used for feeding patients who are unable to take in adequate nutrition by mouth. Unfortunately, these known tubes and devices have no ability to electrically stimulate or "pace" the mucosa of the gastrointestinal tract. Being primarily intended for use as a direct access to the gastrointestinal tract, they lack the flexibility and comprehensive advantages of the present invention.

The structure and operation of a preferred embodiment of the invention having been described above, various individual components may be implemented as follows.

Control and monitoring unit 100 may be adapted from the MEDTRONIC 5375 Demand Pacemaker. This existing pacemaker is manufactured by MEDTRONIC INC., 3055 Old Highway Eight, Post Office Box 1453, Minneapolis, Minn. 55440. Preferably, the electrical pacing stimulus according to the gastrointestinal pacemaker is 1.8 milliseconds, with the pacing rate in a suitable number of pulses per minute (such as 3 PPM) as described above. The stimulus current amplitude adjustment would be from 0.1 to 10 milliamperes. The sensitivity of sensed voltage measurements is from 0.5 to 10 millivolts. The system may be powered by a 9 volt alkaline battery, for example, but a suitable rechargeable battery may also be used.

Elements related to pH sensing measurement and recording, elements 320, 134, 130, 132, 138, 430, may be implemented in a manner similar to the ambulatory pH data recorder Model No. ADR 2200, available from NARCO BIOSYSTEMS, a division of INTERNATIONAL BIOMEDICAL, INC., 8508 Cross Park Drive, Austin, Tex. 78754-4557. In the illustrated embodiment, only the pH electrode 320 is present in the patient's body; however, with continued miniaturization, a recording system can actually be placed through port 232 for local measurement and recordation, and still be readily available for removal if needed.

Stimulative electrodes 312, 314, 316, 318 may be modeled after bipolar electrodes made by CORDIS EUROPA N.V., 9301 LJ Roden, The Netherlands. These electrodes are insulated, the metallic elements being made of gold or platinum. In operation, it is envisioned that the stimulative electrodes 312, 314, 316, 318 would be simultaneously fired through a conductive path through cable 310.

Pressure transducer 332 may be modeled after a SORENSON TRANSPAC II, list 42574-04-14, ABBOTT CRITICAL CARE SYSTEMS, ABBOTT LABS HOSPITAL PRODUCTS DIVISION, North Chicago, Ill. 60064. A TRANSPAC II Disposable Transducer, list 42558-01 MK5-04DTNVF, also available from ABBOTT LABS [list 41233-01, lot 54-028-SN01], may also be used. The system would be filled with fluid, and connected to a pressure transducer for direct readout to a suitable pressure recorder 440. This is in contrast to the illustrated embodiment, in which a local pressure receiver 140 and readout 142 are built into the control and monitoring unit 100.

Modifications and variations of the above-described embodiments of the present invention are possible, as appreciated by those skilled in the art in light of the above teachings. It will readily be appreciated that embodiments of the present invention may be made without using all the elements shown in the drawing figures. For example, fewer or more electrodes may be employed than are illustrated in the drawings. Also, one or more of the pH electrode 320, pressure transducer 332, stimulative electrodes 312, 314, 316, 318, 342, 344, or sensor electrodes 334, 336, may be omitted from a particular embodiment if the patient's medical condition does not warrant such stimulation or monitoring. It is therefore to be understood that, within the scope of the appended claims and their equivalents, the invention may be practiced otherwise than as specifically described.

REFERENCES

1. Sarna S. In vivo myoelectrical activity: methods, analysis, and interpretation. In: Schultz S, Wood JD, eds. *Handbook of Physiology, The Gastrointestinal System*. Baltimore: Waverly Press, 1988:817–863.
2. Hinder RA, Kelly KA. Human gastric pacesetter potential. Site of origin, spread and response to gastric transection and proximal gastric vagotomy. Am J Surgery 1978; 133: 29–33.
3. Koch KL, Stewart WR, Stern RM. Effect of barium meals on gastric electromechanical activity in man. A fluoroscopic-electrogastrographic study. Dig Dis Sci 1987; 32: 1217–1222.
4. Miedema BW, Sarr MG, Kelly KA. Pacing the human stomach. Surgery 1992; 143–50.
5. Koch KL, Stern RM, Stewart WR et al. Gastric emptying and gastric myoelectrical activity in patients with symptomatic diabetic gastroparesis: Effect of long-term domperidone treatment. *Am J Gastxoenterol* 1989; 84:1069–1075.
6. Koch KL, Sperry N, Bingaman S et al. Gastric myoelectrical activity differentiates patients with idiopathic and diabetic gastroparesis from healthy controls. *Gastroenterology* 1990 (abstr); 98:A367.
7. Geldof H, van der Schee EJ, van Blankenstein M, Grashuis JL. Electrogastrographic study of gastric myoelectrical activity in patients with unexplained nausea and vomiting. Gut 1986; 27:799–808.
8. Bisset WM, Devane SP, Milla PJ. Gastric antral dysrhythmias in children with idiopathic intestinal pseudo-obstruction. *J Gastrointestinal Motility* 1989; 1:53 (abstract).
9. Abell TL, Malagelada J-R, Lucas AR et al. Gastric electromechanical and neurohormonal function in anorexia nervosa. *Gastroenterology* 1987; 93:958–965.
10. Geldof H, van der Schee EJ, Smout AJPM et al. Myoelectrical activity of the stomach in gastric ulcer patients: An electrogastrographic study. *J. Gastrointestinal Motility* 1989; 1:122–130.
11. Koch KL, Stern RM, Vasey M, Botti JJ, Creasy GW, Dwyer A. Gastric dysrhythmias and nausea of pregnancy. Dig Dis Sci 1990; 35:961–968.
12. Stern RM, Koch KL, Stewart WR, Lindblad IM. Spectral analysis of tachygastria recorded during motion sickness. Gastroenterology 1987; 93: 92–97.
13. You CH, Lee KY, Chey WR, Dwyer AE. Gastric electromyography in normal and abnormal states in humans. Functional Disorders of the Digestive Tract. Ed. WY Chey, Raven Press, New York, 1983; 167–173.
14. Abell TL, Malagelada J-R. Glucagon-evoked gastric dysrhythmias in humans shown by an improved electrogastrographic technique. Gastroenterology 1985; 88: 1932–1940.
15. Hamilton JW, Bellahsene BE, Richelderfer M, Webster JH, Bass P. Human electrogastrograms: Comparison of surface and mucosal recordings. *Dig Dis Sci* 1986; 31:33–39.
16. Sawchuk A, Canal D, Grosfeld JL, et al. Electrical pacing of the Roux limb resolves delayed gastric emptying. J Surg Res 1987; 42:635–41.
17. Waldhausen J, Courtney T, Schirmer B. Postoperative pacing for gastric antral distension [abstract] J Gastroenterol Mot 1989; 1:66.

What is claimed is:

1. A stimulatory system especially suitable for being placed percutaneously into a subject's gastrointestinal tract, the system comprising:
    means for providing an electrical current;
    means for percutaneously carrying the electrical current through the skin of a subject at a point substantially directly adjacent a portion of the gastrointestinal tract; and
    means for applying the electrical current directly to the inner lining of the gastrointestinal tract from inside the gastrointestinal tract, the means for applying extending, at least in part, in a direction generally perpendicular to a direction of the means for carrying so as to extend substantially away from the means for carrying to allow the means for applying to directly contact the inner lining.
2. The system of claim 1, further comprising:
    means for adjusting the magnitude of the current, to which the means for providing is responsive.
3. The system of claim 1, wherein the means for providing electrical current includes:
    means for providing pulses of electrical current.
4. The system of claim 3, further comprising:
    means for adjusting a repetition rate of the pulses of electrical current, to which the means for providing is responsive.
5. The system of claim 1, wherein the means for applying includes:
    at least one stimulative electrode at the end of at least one respective tentacle shaped for causing the at least one respective stimulative electrode to physically contact the inner lining of the gastrointestinal tract, the at least one tentacle extending generally away from and outside the means for carrying, back in the direction of the inner lining to directly contact the inner lining.

6. The system of claim 1, further comprising:
a pH measurement device, which, when disposed within the gastrointestinal tract, provides an electrical indication of the pH of contents of the gastrointestinal tract.

7. The system of claim 6, further comprising:
means for receiving the electrical indication from the means for measuring the pH, and for providing an indication thereof.

8. The system of claim 1, further comprising:
a pressure measurement device, which, when disposed within the gastrointestinal tract, provides an electrical indication of pressure in the gastrointestinal tract.

9. The system of claim 8, further comprising:
means for receiving the electrical indication from the pressure measurement device, and for providing an indication thereof.

10. The system of claim 8, wherein the pressure measurement device is arranged sufficiently distant from and loosely coupled to the means for carrying electrical signals, so as to adapt the pressure measurement device to be disposed lower in the intestinal tract than the means for carrying electrical signals.

11. The system of claim 1, further comprising:
a muscle electrical activity measurement device, which, when disposed in the gastrointestinal tract, provides an electrical indication of muscle electrical activity.

12. The system of claim 11, further comprising:
means for receiving the electrical indication from the muscle electrical activity measurement device, and for providing an indication thereof.

13. The system of claim 1, wherein the means for applying includes:
at least one stimulative electrode disposed substantially near the means for carrying; and
at least one additional stimulative electrode disposed substantially further from the means for carrying than the at least one stimulative electrode disposed near the means for carrying, the at least one additional stimulative electrode placed at or near the end of a soft member so as to allow the additional stimulative electrode(s) to float lower in the gastrointestinal tract.

14. The system of claim 1, wherein the means for carrying includes:
a flexible tube; and
means for securing the tube in place.

15. The system of claim 14, wherein the means for securing includes:
a mushroom-shaped structure attached to the tube by the gastrointestinal tract and having lateral dimensions larger than the means for carrying.

16. The system of claim 15, wherein the mushroom-shaped structure is soft and compressible.

17. The system of claim 15, wherein the mushroom-shaped structure is firm.

18. The system of claim 1, further comprising:
a port, extending substantially parallel to the means for carrying electrical current, the port constituting a conduit between the outside of the subject and the interior of the gastrointestinal tract, so that materials may be introduced into or removed from the gastrointestinal tract.

19. The system of claim 1, further comprising:
a response sensing device, which, when disposed lower in the gastrointestinal tract than the means for applying, senses gastrointestinal activity occurring in response to the means for applying; and
a delay sensing means for sensing a delay time between (1) application of the electrical current by the means for applying and (2) any sensed gastrointestinal activity from the response sensing device, and for causing the means for providing to immediately provide additional electrical current when no responsive gastrointestinal activity is sensed or when the delay exceeds a predetermined threshold.

20. A method for stimulating muscular activity in a gastrointestinal tract of a subject, comprising the steps of:
inserting percutaneously a device having stimulative electrodes through the subject's skin and into the gastrointestinal tract; and
applying an electrical current to the device to directly electrically stimulate the inner lining of the gastrointestinal tract from inside the gastrointestinal tract.

21. The method of claim 20, further comprising:
adjusting the magnitude of the electrical current.

22. The method of claim 20, further comprising:
adjusting a rate at which pulses of electrical current are provided.

23. The method of claim 20, wherein the applying step comprises:
applying the electrical current as a function of time in a manner causing substantially normal peristalsis in the gastrointestinal tract.

24. The method of claim 20, wherein the inserting step comprises:
inserting a device having one or more stimulative electrodes at or near the end of tentacles which curve back from a percutaneously inserted tube, to touch an inner lining of the gastrointestinal tract.

25. The method of claim 20, wherein the inserting step comprises:
inserting a device having one or more stimulative electrodes at or near the end of tentacles which curve back from a percutaneously inserted tube, loosely coupled to the tube so as to allow the one or more stimulative electrodes to float freely within the gastrointestinal tract.

26. The method of claim 20, wherein the inserting step comprises:
inserting a device having one or more sensor electrodes at or near the end of tentacles which curve back from a percutaneously inserted tube, loosely coupled to the tube so as to allow the one or more sensor electrodes to float freely in a lower portion of the gastrointestinal tract.

27. The method of claim 20, further comprising:
measuring the pH of contents in the gastrointestinal tract; and
providing an indication thereof.

28. The method of claim 20, further comprising:
measuring pressure within the gastrointestinal tract; and
providing an indication thereof.

29. The method of claim 20, further comprising:
measuring electrical muscle activity within the gastrointestinal tract; and
providing an indication thereof.

30. The method of claim 20, further comprising:
sensing a delay between (1) an applied electrical current and (2) a response thereto at a different point in the gastrointestinal tract; and
applying additional electrical current when there is no response within a given time period or when the delay is greater than a predetermined threshold.

* * * * *